United States Patent [19]

Baker et al.

[11] Patent Number: 4,532,257

[45] Date of Patent: Jul. 30, 1985

[54] CERTAIN AURONES AND THEIR USE IN THE TREATMENT OF ALLERGIES

[75] Inventors: Stephen R. Baker, Eversley, England; Terry D. Lindstrom, Indianapolis, Ind.; William B. Jamieson, Woking; William J. Ross, Lightwater, both of England

[73] Assignee: Lilly Industries Limited, London, England

[21] Appl. No.: 556,473

[22] Filed: Nov. 30, 1983

[30] Foreign Application Priority Data

Dec. 4, 1982 [GB] United Kingdom ................. 8234671

[51] Int. Cl.³ ..................... A61K 31/34; C07D 307/83
[52] U.S. Cl. ...................................... 514/470; 549/466
[58] Field of Search .......................... 549/466; 424/285

[56] References Cited

U.S. PATENT DOCUMENTS 4,259,340 3/1981 Baker et al. .......................... 424/285

Primary Examiner—Henry R. Jiles
Assistant Examiner—Bernard I. Dentz
Attorney, Agent, or Firm—James L. Rowe; Arthur R. Whale

[57] ABSTRACT

There are described compounds of the formula

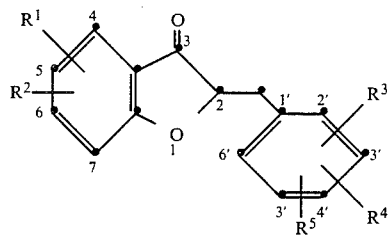

in which either $R^1$ and $R^2$ are both hydrogen or $R^1$ is carboxyl and $R^2$ is hydrogen, $C_{3-4}$alkenyl or $C_{1-4}$alkyl, and $R^3$, $R^4$ and $R^5$ are each hydrogen, nitro, hydroxyl, carboxyl, carboxy$C_{1-2}$alkoxy, $C_{3-4}$alkenyl, $C_{1-4}$alkyl, $C_{3-4}$alkenyloxy, $C_{1-4}$alkoxy or the group

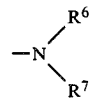

where $R^6$ and $R^7$ are each hydrogen or $C_{1-4}$alkyl; and salts and esters thereof. The compounds are indicated for use in the treatment of immediate sensitivity reactions and inflammatory diseases.

6 Claims, No Drawings

CERTAIN AURONES AND THEIR USE IN THE TREATMENT OF ALLERGIES

This invention relates to novel compounds, to a process for their production and to their use as pharmaceuticals.

British Pat. No. 2,030,142 discloses some aurone compounds having pharmacological properties and of the formula

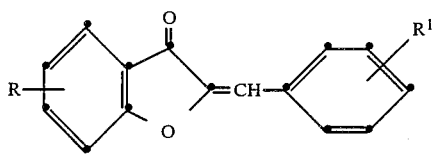

where R and $R_1$ take various substituent values. We have now discovered a group of related compounds which also possess useful pharmacological activity and that can be derived from them.

The compounds of the invention have the formula

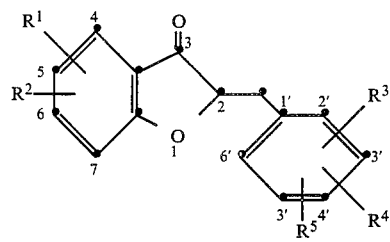

in which either $R^1$ and $R^2$ are both hydrogen or $R^1$ is carboxyl and $R^2$ is hydrogen, $C_{3-4}$alkenyl or $C_{1-4}$alkyl, and $R^3$, $R^4$ and $R^5$ are are each hydrogen, nitro, hydroxyl, carboxyl, carboxy$C_{1-2}$alkoxy, $C_{3-4}$alkenyl, $C_{1-4}$alkyl, $C_{3-4}$alkenyloxy, $C_{1-4}$alkoxy or the group

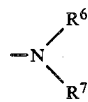

where $R^6$ and $R^7$ are each hydrogen or $C_{1-4}$alkyl; and salts and esters thereof.

In the above formula when reference is made to $C_{1-4}$alkyl both branched and unbranched alkyl groups are included and for example preferred groups are methyl, ethyl, propyl, isopropyl, butyl and tert.butyl. Similarly $C_{3-4}$alkenyl includes both branched and unbranched groups and a preferred example is allyl. Alkenyloxy and alkoxy are such groups attached via an oxygen atom to the nucleus. The term, carboxy-$C_{1-2}$alkoxy, covers carboxymethoxy, 2-carboxyethoxy and 1-carboxyethoxy.

A preferred group of compounds is one of formula (I) above, in which $R^1$ is carboxyl (especially in the 5-position), $R^2$ (especially in the 7-position) is hydrogen, $C_{3-4}$alkenyl or $C_{1-4}$alkyl, and $R^3$, $R^4$ and $R^5$ are each hydrogen, hydroxyl, $C_{3-4}$alkenyl, $C_{1-4}$alkyl, $C_{3-4}$alkenyloxy, $C_{1-4}$alkoxy or the group

when $R^6$ and $R^7$ are each hydrogen or $C_{1-4}$alkyl.

A further preferred group of compounds is one of the formula (I), in which $R^1$ is carboxyl (especially those substituted in the 5-position), $R^2$ is hydrogen and $R^3$, $R^4$ and $R^5$ are each hydrogen, carboxyl, $C_{1-4}$alkyl or $C_{1-4}$alkoxy.

Suitable salts of compounds of invention include for example, those of mineral bases such as alkali metal hydroxides, especially the potassium or sodium salts, or alkaline earth metal hydroxides, especially the calcium salts, or of organic bases such as amines of the type $HNR^6R^7$ or tetriary amines $NR^6R^7R^8$ where $R^8$ is $C_{1-4}$alkyl. When the compounds contain an amino group or a basic nitrogen, acid addtion salts are included such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic or naphthalene-2-sulphonic acid. Preferred esters are those derived from $C_{1-12}$alkanols giving a $C_{1-12}$alkyl ester and especially $C_{1-4}$alkanols and, for example the methyl, ethyl, propyl, isopropyl and n-butyl esters. Also included are esters having a substituted alkyl group in view of the fact that it is often desirable to attach an ester group that cleaves to give the free acid. Examples of such substituted alkyls include acetoxymethyl, methylthiomethyl, methoxyethyl, ethoxyethyl, methylsulphinylmethyl and methylsulphonylmethyl and $C_{1-12}$alkyl groups substituted by a —$NR^6R^7$ group such as for example 2-dimethylaminoethyl or 2-diethylaminoethyl.

The preferred salts and esters are those which are pharmaceutically-acceptable but other derivatives are also included in the invention since they may be useful as intermediates in the preparation, purification or characterisation of the pharmaceutical end product.

The invention includes a method of preparing compounds of formula (I) which comprises reducing a compound of the formula

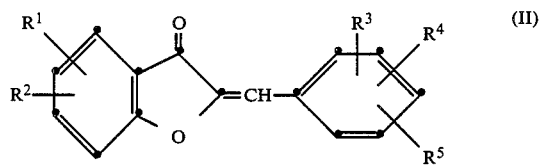

(II)

The reduction is preferably carried out by the use hydrogen and a metal catalyst, the latter preferably being a precious metal such as platinum or palladium. It has been found that 10 percent palladium on charcoal is a convenient catalyst for this purpose. Generally the reduction process is carried out in a solvent such as an inert organic solvent, for example, acetic acid, and at a temperature from 0° C. to 100° C., for example at room temperature.

As mentioned above, the compounds of formula (II) are known and their method of preparation is described, for example, in British Pat. Nos. 2,030,142, 2,014,566 and 2,001,631. They may best be prepared by condensing an appropriately substituted benzaldehyde with a benzofuranone as depicted below:

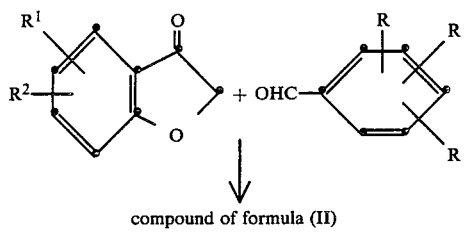

compound of formula (II)

It will be appreciated that compounds of formula (I) have an asymmetric centre at the carbon atom of the benzofuranone moiety linked to the benzyl group (carbon number 2) and this asymmetry gives rise to the existance of optical isomers. Substantially pure optical isomer can be prepared by chemical reaction in the presence of a chiral catalyst. Alternatively, a racemic mixture of both isomers can be separated by conventional chemical methods such as for example by the preparation of diastereoisomers as salts with an optically-active base and subsequent liberation of the enantiomers.

The anti-allergy activity of the compounds according to formula (I) and their pharmaceutically acceptable salts and esters has been demonstrated in guinea pigs using either the "guinea-pig chopped lung test" described by Mongar and Schild in the Journal of Physiology (London) 131, 107(1956) or Brocklehurst in the Journal of Physiology (London) 151, 416 (1960), or the "Herxheimer" test described in the Journal of Physiology (London) 117, 251(1952). In the "Herxheimer" test, which is based on an allergic bronchospasm induced in guinea pigs closely resembling an asthmatic attack in man, compounds exhibited activity at dosages ranging from 25 mg/kg to 200 mg/kg.

The compounds of the invention have also shown activity in tests devised to indicate anti-inflammatory activity as, for example, the adjuvant arthritis test (B. B. Newbould Chemotherapy of Arthritis Induced in Rats by Mycobacterial Adjuvant. Br. J. Pharmacol. 21, 127–136 (1963)).

The compounds of this invention are accordingly indicated for therapeutic use in the treatment of immediate sensitivity reactions and in particular in the treatment of asthma, as well as being of use in the treatment of anti-inflammatory diseases.

The compounds of this invention may be administered by various routes, for example, by the oral or rectal route, by inhalation, topically or parenterally, for example by injection, being usually employed in the form of a pharmaceutical composition. Thus the invention includes a method of administering a compound according to formula I to a mammal suffering from an allergic reaction or an inflammatory disease or to prevent such allergic or inflammatory disease. Pharmaceutical compositions also form part of the present invention and are prepared in a manner well known in the pharmaceutical art and normally comprise at leat one active compound in association with a pharmaceutically acceptable diluent or carrier. In making the compositions of the present invention, the active ingredient will usually be mixed with a carrier, or diluted by a carrier, and/or enclosed within a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixires, suspensions, aerosols as a solid or in a liquid medium, ointments for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 g, more usually 25 to 200 mg, of the active ingredient. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall withing the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The following Example illustrates the invention.

EXAMPLE (a)

Z-3-[(2,3-Dihydro-5-methoxycarbonyl-3-oxo-2-benzofuranyl)methylene]benzoic acid

5-Methoxycarbonylbenzofuran-3-(2H)one (4.9 g) was dissolved in warm dioxan (50 ml). 3-Carboxybenzaldehyde (4.5 g) was then added followed by concentrated hydrochloric acid (10 ml). The mixture was heated on a steam bath for 15 minutes with formation of yellow crystals. After cooling and addition of an equal volume of water, the crystalline product was filtered off and recrystallised from dimethylformamide to give the title compound, m.p. 280° C.

(b)

3-[(2,3-Dihydro-5-methoxycarbonyl-3-oxo-2-benzofuranyl)methyl]benzoic acid

The product from (a) (1 g) was suspended in glacial acetic acid (100 ml) and hydrogenated at 60 p.s.i. in the presence of 10% palladium on carbon (100 mg). After 1 hour the catalyst was filtered off and the colourless filtrate evaporated in vacuo to give a light straw coloured oil which crystallised on standing. Recrystallisation from ethyl acetate/petrol gave the required product as off-white crystals, m.p. 140°-143° C.

We claim:

1. A compound of the formula

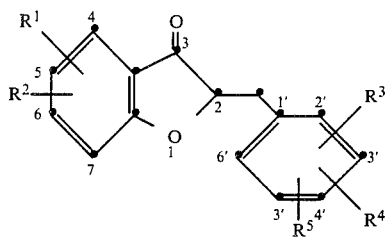

in which $R^1$ is carboxyl and $R^2$ is hydrogen, $C_{3-4}$alkenyl or $C_{1-4}$alkyl, and $R^3$, $R^4$ and $R^5$ are each hydrogen, nitro, hydroxyl, carboxyl, carboxy$C_{1-2}$alkoxy, $C_{3-4}$alkenyl, $C_{1-4}$alkyl, $C_{3-4}$alkoxy or the group

where $R^6$ and $R^7$ are each hydrogen or $C_{1-4}$alkyl; and pharmaceutically-acceptable acid addition salts and the $C_{1-12}$alkyl, 2-dimethylaminoethyl, 2-diethylaminoethyl or substituted methyl or ethyl esters thereof, where said substituents are members of the group acetoxy, methylthio, methoxy, ethoxy, methylsulfinyl and methylsulfonyl.

2. A compound according to claim 1 in which $R^1$ is carboxyl, $R^2$ is hydrogen and $R^3$, $R^4$ and $R^5$ are each hydrogen, carboxyl, $C_{1-4}$alkyl or $C_{1-4}$alkoxy.

3. A compound according to claim 1 in which $R^1$ is carboxyl in the 5-position, $R^2$ is hydrogen and $R^3$, $R^4$ and $R^5$ are each hydrogen, carboxyl, $C_{1-4}$ alkyl or $C_{1-4}$ alkoxy.

4. A pharmaceutical composition in unit dosage form containing per unit dosage an antiallergic amount of a compound according to claim 1 effective to treat an allergy and a pharmaceutically-acceptable diluent or carrier therefor.

5. A method of treating a mammal including a human, suffering from an allergy disorder which comprises administering an effective amount of a compound according to claim 1.

6. A method of treating a mammal including a human, suffering from an inflammatory disorder which comprises administering an effective amount of a compound according to claim 1.

* * * * *